United States Patent [19]

van den Bergh et al.

[11] Patent Number: 5,068,515
[45] Date of Patent: Nov. 26, 1991

[54] APPARATUS FOR HOMOGENIZING THE NON-HOMOGENEOUS LIGHT DISTRIBUTION OF A LASER BEAM

[75] Inventors: Hubert van den Bergh, Goumoens-la-Ville; Peter F. Cornaz, deceased, late of Vevey; Max M. Cornaz, heir, Chesalles; Jean-Pierre Cornaz, heir, Pratteln; Maria I. Cornaz, heir, Berne; Georges Wagnières, Lutry, all of Switzerland

[73] Assignee: Ciba-Geigy Corporation, Ardsley, N.Y.

[21] Appl. No.: 630,120

[22] Filed: Dec. 19, 1990

[30] Foreign Application Priority Data

Dec. 27, 1989 [CH] Switzerland ............... 4652/89

[51] Int. Cl.⁵ .................................. B23K 26/06
[52] U.S. Cl. ...................... 219/121.73; 219/121.75
[58] Field of Search ............... 219/121.73, 121.78

[56] References Cited

U.S. PATENT DOCUMENTS 4,482,214 11/1984 Hill et al. ........................... 350/355
4,681,396 7/1987 Jones .................................. 350/96.18
4,733,047 3/1988 Cruickshank et al. ........ 219/121.63

FOREIGN PATENT DOCUMENTS 0184643 7/1987 European Pat. Off. .
2455300 11/1980 France .

Primary Examiner—C. L. Albritton
Attorney, Agent, or Firm—Harry Falber

[57] ABSTRACT

An apparatus for precise, homogeneous and sharp-edged irradiation of a large area with the light of a laser beam (5), which can be used especially for large-area photodynamic therapy, is provided with a multimode fibre (10), which is illuminated by the laser beam by way of a microscope objective (4) and has a length of approximately 5 meters, and the end face (13) of which is imaged onto an irradiated area (7) of a working surface (6) by means of a microscope (17).

9 Claims, 1 Drawing Sheet

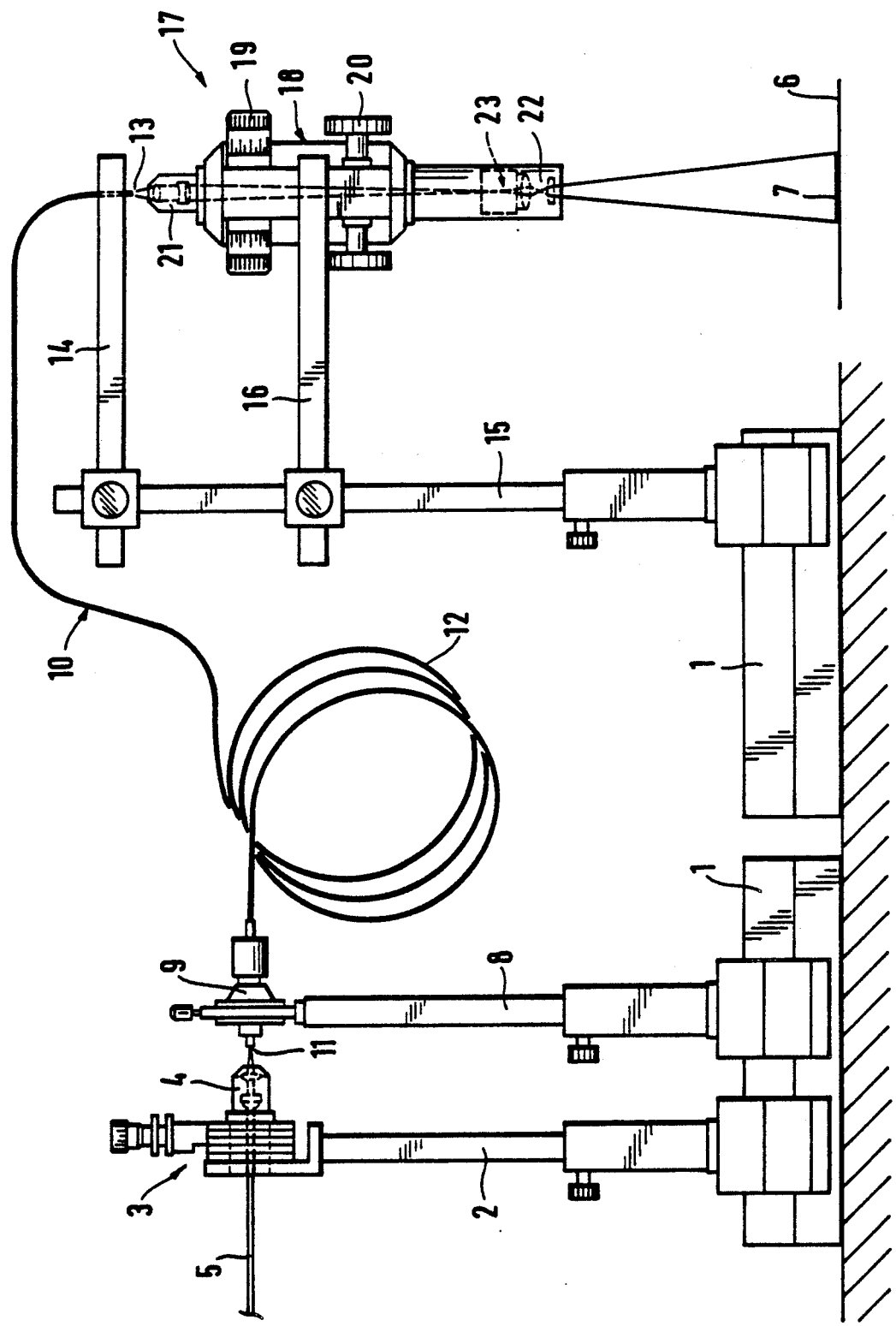

APPARATUS FOR HOMOGENIZING THE NON-HOMOGENEOUS LIGHT DISTRIBUTION OF A LASER BEAM

The invention relates to an apparatus for homogenising the non-homogeneous light distribution of a laser beam for the sharp-edged irradiation of an area, having an optical arrangement struck by the laser beam that contains a multimode fibre.

It is known to concentrate the light of a laser using an optical fibre, for example a multimode fibre, and bring it to a site remote from the laser in order to illuminate that site with the light discharging from the end face of the multimode fibre. A system suitable for that purpose, which is used for material processing, is described in U.S. Pat. No. 4,681,396. In that system, the laser beam emerging from a laser is focussed onto the core of the inlet end of an optical fibre and in that manner fed into the fibre core. Once the light has passed through the fibre it passes out again through the outlet end of the fibre and is focussed onto the material to be processed; the dimensions of the light spot are therefore very small. Furthermore, in that system, as in other conventional arrangements, the laser beam, which diverges when it emerges at the outlet end face of the multimode fibre, has a non-homogeneous distribution of intensity, the intensity being at its greatest along the axis of the laser beam and gradually dropping towards the sides. For the photodynamic therapy of skin cancer and for in vitro irradiation of cell cultures, however, in order to obtain constant results that can readily be reproduced, uniform and precise irradiation of an area that is large in comparison with the end face of a multimode fibre is desirable. A sharp drop in light intensity at the sides of the beam is necessary, especially when the selectivity of the chemical substance used is low, in order to avoid damage to the healthy tissue adjacent to the tumour. In addition, light energy is saved in this manner.

The problem underlying the invention is to provide an apparatus of the kind mentioned at the beginning that permits very uniformly distributed and very precisely localised irradiation of an area that is large in comparison with the cross-sectional area of a multimode fibre with an optical dosage.

This problem is solved in accordance with the invention as follows: the optical arrangement has a multimode fibre several meters in length, the inlet end face of which is struck by a laser beam focussed by means of focussing optics and the outlet end face of which can be imaged onto the area to be irradiated using strongly magnifying projection optics.

As a result of the fact that the outlet end face is not brought right up to the area to be irradiated, it is possible to illuminate a larger area, the projection optics ensuring sharp-edged illumination by projecting an image of the outlet end face onto the area to be irradiated. The outlet end face and the area to be irradiated are illuminated very homogeneously because mode mixing occurs in the several meters' length of the multimode fibre, so that there is a homogeneous distribution of energy over the cross-section of the end of the multimode fibre.

The apparatus according to the invention permits short irradiation distances, which is very helpful in many clinical situations.

In an advantageous embodiment of the invention, the projection is effected by means of a microscope having an objective which is arranged in such a manner a short distance in front of the end face of the multimode fibre that the longitudinal axis of the multimode fibre is in alignment with the longitudinal axis of the microscope objective. The microscope objective is an objective having a larger numerical aperture than that of the multimode fibre, preferably an objective having a numerical aperture of approximately 0.45, which permits the production of an intermediate image, magnified by a factor of ten to a hundred, especially twenty, of the outlet end face of the multimode fibre. In one embodiment of the invention, the intermediate image is then projected, by means of the eyepiece of the microscope, with a magnification of 12 onto the area to be irradiated so that, with a core diameter of 200 micrometers for the multimode fibre, a disc of 4.8 cm diameter is illuminated with a rectangular intensity distribution.

The focussing optics used to feed in the laser light may be a microscope objective having a numerical aperture of 0.45 and a magnification factor of 20. In order to obtain a sharp image on the area to be illuminated and to compensate for variations in distance, the microscope is provided with means for coarse adjustment and fine adjustment. The projection optics, together with the portion of the multimode fibre containing the outlet end face, are secured to a holding means that is axially displaceable with respect to the area to be illuminated in order to set the predetermined distance for a predetermined size of illuminated area.

The multimode fibre is preferably coiled into a space-saving spiral in a central portion. A particularly high degree of homogeneity of irradiation dosage can be achieved by the use of a vibration means that causes flexional vibrations of the multimode fibre in a portion between the front face and the end face of the multimode fibre. Such a vibration means may consist of a shaft executing a reciprocal rotary vibration, the longitudinal axis of which runs parallel to a short portion of the multimode fibre and the free end of which is joined to the cladding of the multimode fibre. As a result of the vibration and the shaking, by averaging out over time the speckles are homogenised and thus also a high degree of homogeneity of the optical dosage is achieved over relatively shorter irradiation times. To the eye of an observer, there is a homogeneous speckle-free impression if the frequency of the vibration exceeds the resolution power of the eye in respect of time.

The invention is described in detail in the following with reference to the drawings, comprising only one Fig., which is a diagrammatic representation of a lateral view of the apparatus for homogenising the optical dosage in large-area irradiation.

The drawing shows rails of an optical bench 1, which can be used to erect the apparatus for homogeneous irradiation of a large area. A first holder 2 on the optical bench 1 carries an XY positioning means 3 for the holder of a microscope objective 4 which, for example, has a numerical aperture of 0.45 and a magnification of 20.

The microscope objective 4 is used to focus a laser beam 5, the intensity distribution of which in cross-section is generally bell-shaped, so that the intensity is at its greatest in the middle of the laser beam and gradually falls towards the periphery. The apparatus illustrated in the drawing serves to convert the bell-shaped intensity distribution over the cross-section of the narrow laser beam in such a manner that on the working surface 6 an irradiated area 7 with a diameter of several centimeters is homogeneously uniformly illuminated and at the periphery of the irradiated area there is a sudden drop in intensity corresponding to a rectangular intensity distribution.

A second holder 8 on the optical bench 1 is provided with an XY-positioning means having a fibre holder 9 for the first end of a multimode fibre 10. The multimode fibre 10 has, for example, a core diameter of 200 micrometers and a cladding diameter of 280 micrometers. Its numerical aperture is approximately 0.21. Especially homogeneous illumination of the area 7 is obtained if a stepped index fibre is used.

The inlet end face 11 of the first end of the multimode fibre clamped in the fibre holder 9 is disposed at a distance from the microscope objective 4 that is slightly greater than the distance of the narrowest point of the focussed laser beam emerging from the microscope objective 4 so as to permit optimum light input and adjustment.

The light energy fed into the end face 11 is transmitted in the multimode fibre 10, which, for example, is approximately 5 meters long and a portion of which may be in the form of a spiral 12. As a result of the great length and the bends of the multimode fibre 10, a mixing of modes occurs in the core thereof, so that a uniform distribution of light intensity over the cross-sectional area of the core of the multimode fibre 10 can be observed at the outlet end face 13 of the multimode fibre 10.

An especially high mean homogeneity can be achieved by averaging out the speckles over time by setting the stepped index fibre or multimode fibre 10 vibrating, especially with flexional vibrations, in the region of the spiral 12 or at another position, by means of a vibrator not shown in the drawing. The vibrator may be arranged, for example, in the middle of the multimode fibre 10 and have an electrically operated shaft executing a reciprocal rotary vibration of which the end extending parallel to the multimode fibre 10 is mechanically coupled to the cladding of the multimode fibre 10. The drive of an electric toothbrush, which is battery-operated and consequently compact and independent of the rest of the arrangement, may be used as a means for such a further improvement in the homogeneity of the light distribution at the end face 13 by elimination of the speckles.

The cladding of the multimode fibre 10 can be joined to the rotary vibrating journal of the toothbrush drive by a strip of a few centimeters' length, which at one end is fixed to the journal of the toothbrush and at the other end is provided with a clamp, causing the cladding of the multimode fibre 10 to vibrate when the toothbrush drive is in operation.

The second end of the multimode fibre 10 with the end face 13 is fastened in an arm 14 held by a third holder 15 on the optical bench 1. The third holder 15 furthermore has an extension arm 16, which is joined to the housing and the body 18 of a microscope 17, which is provided in customary manner with a wheel drive 19 for fine adjustment and a wheel drive 20 for coarse adjustment.

Indicated in the drawing in the microscope 17 are the positions of several lenses and of the path of rays. The microscope 17 is provided with an objective 21, the inlet lens of which, depending on the focal length thereof, is arranged at a distance of from 1 to 100 mm, especially from 1 to 2 mm, from the end face 13 of the multimode fibre 10. The objective 21 has, for example, a numerical aperture of 0.45 and produces in the vicinity of the eyepiece 22 of the microscope 17 an intermediate image 23, which is magnified by a factor of 20 by comparison with the end face 13 imaged by the objective 21. Since the core of the multimode fibre 10 is uniformly illuminated, whilst the front face of the cladding of the multimode fibre 10 remains dark, the intermediate image 23 viewed in the radial direction has a rectangular light intensity distribution corresponding to that directly on the end face 13 of the multimode fibre 10.

The intermediate image 23 and thus the end face 13 of the multimode fibre 10 is projected by means of the eyepiece 22 of the microscope 17 in the form of an irradiated area 7 on the working surface 6. If the eyepiece 22 of the microscope has a magnification of 12, the microscope 17 thus permits projection of an image of the outlet end face 13 of the multimode fibre 10 onto the working surface 6 with a total magnification of 240. With a core diameter of 200 micrometers, the irradiated area 7 has a diameter of 4.8 centimeters. The light incidence on the irradiated area 7 is substantially perpendicular. The optical dosage is very uniformly distributed and decreases suddenly at the periphery of the irradiated area 7. In this manner, the optical dosage can be very precisely uniformly and reproducibly localised. The perpendicular to the irradiated area 7 is in alignment with the longitudinal axis of the microscope 17 and with the perpendicular to the end face 13 at that end of the multimode fibre 10 which is clamped in the arm 14.

In order to obtain an accurate alignment of the longitudinal axis of the multimode fibre 10 in the region of the end face 13 and an end face 13 aligned at right angles to the longitudinal axis of the objective 21, the arm 14 is provided with a suitable holding device not shown in the drawing.

The person skilled in the art can see from the above description that the basic concept of the apparatus consists in producing an image of the homogeneously irradiated end face 13 of the multimode fibre 10, especially a stepped index fibre, on the working surface 6, which is the surface of the skin of a patient or of an animal or an area in a petri dish.

What is claimed is:

1. Apparatus for homogenising the non-homogeneous light distribution of a laser beam for the sharp-edged irradiation of an area, having a laser beam source, focusing optics for focussing the laser beam, an optical arrangement positioned after said focussing optics having a multimode fibre (10) with an inlet end face and an outlet end face, and magnifying projection optics positioned after said outlet end face, the inlet end face (11) being struck by the laser beam (5) focussed by means of the focussing optics (4) and the outlet end face (13) being imaged onto the area (6, 7) to be irradiated by means of the magnifying projection optics (17).

2. Apparatus according to claim 1, wherein the magnifying projection optics is a microscope (17) having the objective (21) arranged a short distance beyond the outlet end face (13) of the multimode fibre (10) and longitudinal axes aligned with one another.

3. Apparatus according to claim 2, wherein the multimode fibre (10) has a core diameter of 200 micrometers and the objective (21) of the microscope (17) has a numerical aperture of 0.45.

4. Apparatus according to claim 3, wherein the microscope objective (21) is positioned to produce an intermediate image (23) of the outlet end face (13) of the multimode fibre (10), said intermediate image (23) being magnified by a factor of twenty, and wherein the eyepiece (22) of the microscope (17) is positioned to project said intermediate image (23) with a magnification factor of 12 onto the area (6,7) to be irradiated.

5. Apparatus according to claim 1, wherein the focussing optics for focussing the laser beam is a microscope objective (4) having a numerical aperture of 0.45 and a magnification factor of 20.

6. Apparatus according to claim 2, wherein the microscope (17) has means (19,20) for coarse adjustment and fine adjustment.

7. Apparatus according to claim 1, wherein the magnifiyng projection optics (17), together with the portion of the multimode fibre (10) containing the outlet end face (13), are secured to a holding means (14, 15, 16) that is axially displaceable with respect to and parallel to the irradiated area (6,7).

8. Apparatus according to claim 1, wherein a portion of the multimode fibre (10) is coiled in the form of a spiral (12).

9. Apparatus according to claim 1, wherein a portion of the multimode fibre (10) lying between the inlet end face (11) and the outlet end face (13) is mechanically coupled to a vibration means.

* * * * *